US00PP12349P2

(12) United States Plant Patent
Shibamichi

(10) Patent No.: US PP12,349 P2
(45) Date of Patent: Jan. 8, 2002

(54) *CAMELLIA ROSTHORNIANA* PLANT NAMED 'ELINA'

(75) Inventor: Akira Shibamichi, Saitama Prefecture (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 09/599,684

(22) Filed: Jun. 22, 2000

(51) Int. Cl.[7] ..... A01H 5/00
(52) U.S. Cl. ..... Plt./244
(58) Field of Search ..... Plt./243, 244

*Primary Examiner*—Bruce R. Campell
*Assistant Examiner*—June Hwu
(74) *Attorney, Agent, or Firm*—Christie, Parker & Hale, LLP

(57) ABSTRACT

A new plant variety of *Camellia rosthorniana* characterized by its upright growth habit and large flowers with reddish-pink colored outer petals.

4 Drawing Sheets

BACKGROUND OF THE INVENTION

The present invention relates to a new and distinct variety of *Camellia rosthorniana*, which was discovered in 1991 as a seedling selection in a controlled planting of *Camellia rosthorniana* (unpatented) in Kawasguchi City, Japan. The varietal denomination of the new variety is 'ELINA'.

The genus Camellia is included in the family Theaceae which comprises about 25 genera shrubs and trees, mostly tropical and subtropical in origin, and native to the northern and southern hemispheres. Camellia comprises more than 80 species of evergreen shrubs or trees, many of which possess desirable ornamental characteristics.

*Camellia rosthorniana* Hand.-Mazz (1925) is a shrub growing 3 m tall, generally having narrow to broad elliptic leaves with blunt to long acuminate apices, 2.5 to 4.2 cm long and 9 to 18 mm wide. Flowers are white, pedicellate, 1.1 to 1.4 cm across, with 5 to 7 petals. *Camellia rosthorniana* is a shrub widespread and common throughout Guizhou and Guangxi, Sichuan, Yunnan Provinces, China. The plant is evergreen. Leaf color is dark green depending on light intensity.

SUMMARY OF THE INVENTION

The new variety was discovered as a seedling in a controlled planting of *Camellia rosthorniana* and differs from its parent in having pink flower buds as well as pink at the base of the encasing exterior flower petals, and larger flowers and an upright growth habit with significantly smaller leaves than the species. Asexual reproduction of the new variety by stem cuttings performed in Saitama Prefecture, Japan; Lewisberry, Pa.; Vacaville, Calif.; Irvine, Calif.; and Fulshear, Tex.; have confirmed that the distinctive characteristics of the new variety are stable and transmitted to succeeding generations.

COMPARISON WITH PARENT

'ELINA' is distinguished from its parent and all other varieties of *Camellia rosthorniana* of which I am aware in its production of attractive pink buds and flowers with reddish-pink colored outer petals, as well as larger flowers and smaller leaves than the parent.

DESCRIPTION OF ILLUSTRATIONS

The accompanying illustrations show a specimen of the new variety in photographic illustration as true to color as is reasonably possible to make in illustrations of this character.

DETAILED DESCRIPTION OF THE NEW VARIETY

Figure 1:
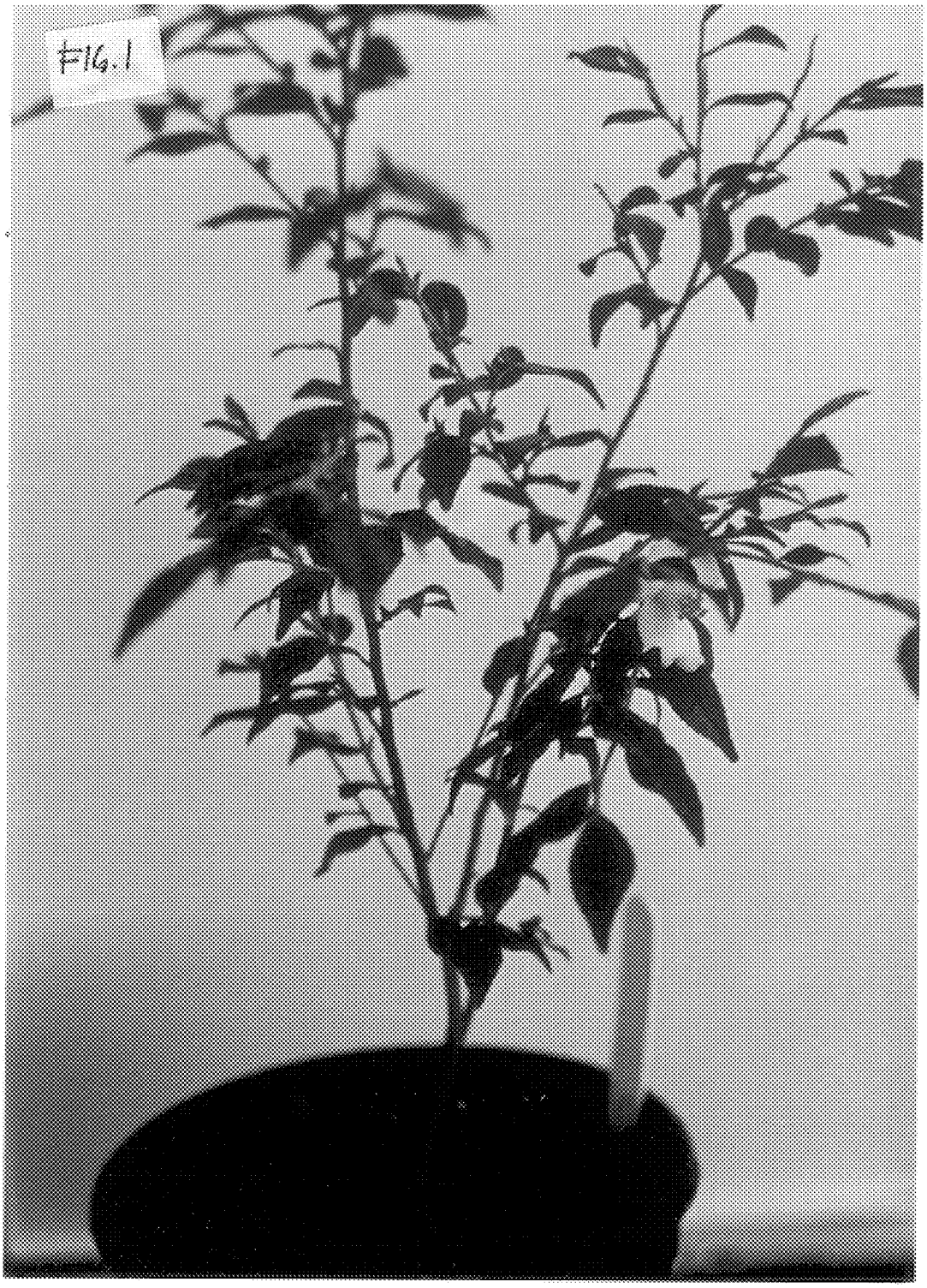
FIG. 1 illustrates the variety in bloom and the upright growth habit and the distinct pink inflorescence.
Figure 2:
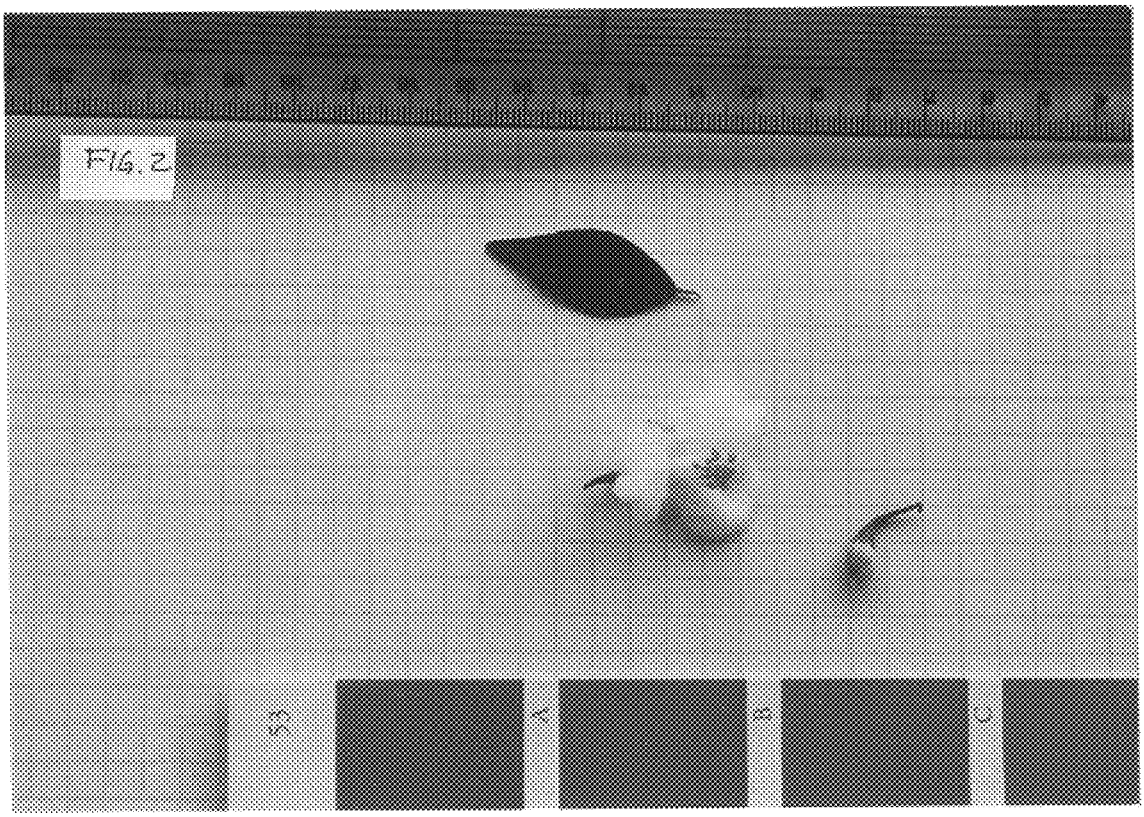
FIG. 2 illustrates the flower bud with the pink coloration when closed as well as the smaller leaf and open flower front view in approximate scale of the flower bud to the plant.
Figure 3:
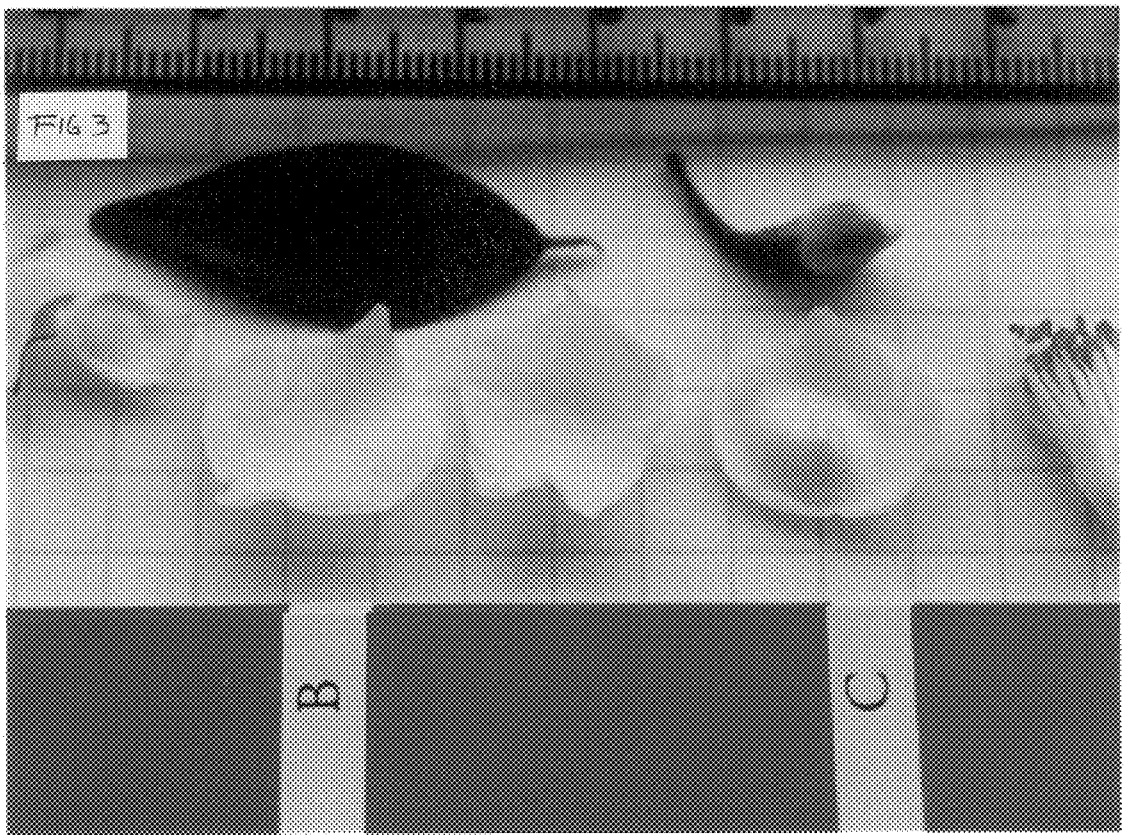
FIG. 3 illustrates the flower parts and shows that the outer flower petals have pink coloration while the inner ones only exhibit a slight pink coloration, but are primarily white.
Figure 4:
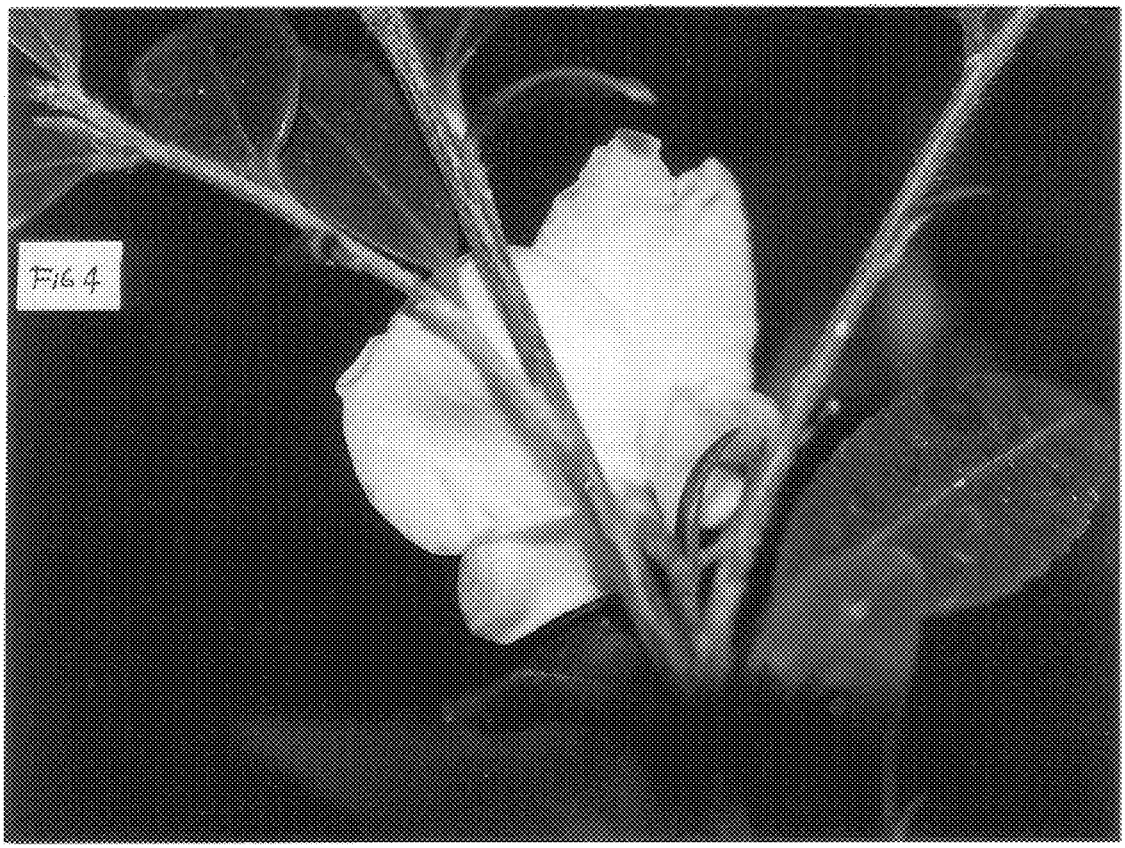
FIG. 4 illustrates the flower bud when open with the pink coloration of the outer flower petals.

'ELINA' has not been observed under all possible environmental, cultural and light conditions. The following observations and descriptions are of 2-year-old plants, in 5-gallon nursery containers, grown in an unheated greenhouse under 70% shade during summer months, in a production nursery setting in Vacaville, Calif. In this description, color references are to The Royal Horticultural Society Colour Chart (1995) and terminology used in the color descriptions herein refers to plate numbers in this color chart. Phenotypic expression may vary with light intensity, cultural, and environmental conditions.

CLASSIFICATION

Botanical: *Camellia rosthorniana* 'Elina'.
Parentage: Chance seedling in a controlled planting of *Camellia rosthorniana* (unpatented).
Propagation: By stem cuttings.

PLANT

Size: Mature plant can grow to approximately 3 m tall and approximately 2 m wide.
Habit: Upright evergreen shrub.
Leaves: Simple, entire.
*Size.*—Average about 2.5 to 4.5 cm long and about 1 to 2 cm wide.

*Shape.*—Elliptic.
*Apex.*—Acuminate.
*Base.*—Attenuate.

Color:
*New growth.*—Upper side: Near Greyed-Purple Group 183A. Under side: Near Green Group 138A.
*Mature growth.*—Upper side: Near Green Group 139A. Under side: Near Green Group 137C.

Texture:
*New growth.*—Upper side: Hirsute. Under side: Hirsute.
*Mature growth.*—Upper side: Glabrous. Under side: Glabrous.

Leaf margin: Serrate to serrulate, slightly turned down at the edges.

Venation: Reticulate.

Petioles:
*Length.*—About 2 to 4 mm long.
*Color.*—Near Grey-Brown Group 199A.

Branching: Over all habit of the plant is upright. The new growth towards the apex of the plant grows upward at about a 45° angle.

Stems:
*Color.*—Ranging from near Grey-Brown Group 199A to 199C.
*Texture.*—Hirsute.

Hardiness: USDA Zone 8 (10° to 20° F.).

Vigor: Approximately 18" over 12-month period on young plants, slowing as plant matures.

Pests/diseases: None noted.

INFLORESENCE

Bloom period: Early February through early April.

Flower form: Solitary at the leaf axils; campanulate at anthesis, petals spreading as the flower ages, becoming salviform; triangular, comprising 3 nearly identical petals subtended by 2 smaller petals.

Flower arrangement: Pedicellate; pendant flowers outfacing at about a 90° angle from the stem.

Flower size: In bud, approximately 1 cm long and 6 mm in circumference; when open, approximately 2.5 to 3 cm across.

Fragrance: None noted.

Lastingness of individual blooms: From 1 to 2 weeks; self-cleaning.

Petals:
*Outer petals.*—Shape: Ovate to rounded ovate, concave, arranged alternately between inner petals. Size: Approximately 7 mm long and 5 mm wide. Color: In bud, the 2 outer petals are near Red Group 53C; as bud expands, outer petals retain near reddish-pink color 53C at apex, but base of petal (lower one-quarter to one-third) is near White Group 155C.
*Inner petals.*—Shape: Ovate to obovate in outline; deeply notched at the apex; petal margins slightly wavy. Size: 3 inner petals roughly equal in size, larger than the 2 outer petals, approximately 1.25 to 1.5 cm long and 1.0 to 1.2 cm wide. Color: Near White Group 155C. Flower sepals: Slightly cupped, pointed to about 1 mm long.

REPRODUCTIVE ORGANS

Androecium:
*Stamens.*—Number: About 23 to 28. Size: Approximately 10 mm long. Style Color: Near White Group 155C. Anther Color: Near Yellow-Orange Group 22A. Pollen Color: Near Yellow-Orange Group 21B.

Gynoecium:
*Pistil size.*—Approximately 12 mm long.
*Fruit type.*—Elliptical; about 3 or 4 segments. Length: Approximately 2 cm. Diameter: Approximately 14 mm. Color: Near Greyed-Orange Group 175B. Seed: None observed.

I claim:

1. A new *Camellia rosthorniana* variety of the plant substantially as shown and described.

* * * * *

B
C